(12) United States Patent
Skarping et al.

(10) Patent No.: US 9,329,066 B2
(45) Date of Patent: May 3, 2016

(54) FLOW REGULATING SYSTEM AND MONITORING DEVICE COMPRISING SAID FLOW REGULATING SYSTEM FOR THE DETECTION OF AIR BORNE ANALYTES

(75) Inventors: Gunnar Skarping, Haessleholm (SE); Marianne Dalene, Haessleholm (SE)

(73) Assignee: Provtagaren AB, Hassleholm (SE)

(*) Notice: Subject to any disclaimer, the term of this patent is extended or adjusted under 35 U.S.C. 154(b) by 831 days.

(21) Appl. No.: 13/581,539

(22) PCT Filed: Mar. 1, 2011

(86) PCT No.: PCT/SE2011/050232
§ 371 (c)(1),
(2), (4) Date: Aug. 28, 2012

(87) PCT Pub. No.: WO2011/108981
PCT Pub. Date: Sep. 9, 2011

(65) Prior Publication Data
US 2012/0329166 A1    Dec. 27, 2012

Related U.S. Application Data

(60) Provisional application No. 61/309,123, filed on Mar. 1, 2010.

(51) Int. Cl.
| | | |
|---|---|---|
| *G01F 1/72* | (2006.01) | |
| *G01F 1/68* | (2006.01) | |
| *G01F 15/04* | (2006.01) | |
| *G01N 35/00* | (2006.01) | |
| *G01N 1/40* | (2006.01) | |
| *G01N 30/72* | (2006.01) | |
| *G01N 30/12* | (2006.01) | |

(52) U.S. Cl.
CPC .. *G01F 1/72* (2013.01); *G01F 1/68* (2013.01); *G01F 15/046* (2013.01); *G01N 35/00693* (2013.01); *G01N 1/405* (2013.01); *G01N 30/7206* (2013.01); *G01N 2030/126* (2013.01); *Y10T 436/17* (2015.01)

(58) Field of Classification Search
CPC ............ G01F 15/046; G01F 1/68; G01F 1/72
USPC .................................................. 700/282, 283
See application file for complete search history.

(56) References Cited

U.S. PATENT DOCUMENTS

| 5,524,084 A | 6/1996 | Wang et al. |
|---|---|---|
| 5,892,160 A | 4/1999 | Hall |

(Continued)

FOREIGN PATENT DOCUMENTS

| EP | 1 793 209 | 6/2007 |
|---|---|---|
| JP | 2002-352839 | 12/2002 |
| JP | 2008-002864 | 1/2008 |

*Primary Examiner* — Lisa Caputo
*Assistant Examiner* — Punam Roy
(74) *Attorney, Agent, or Firm* — Preti Flaherty Beliveau & Pachios LLP

(57) ABSTRACT

A flow regulating system for maintaining a stable air flow comprising at least one pump, a mass flow sensor, an ambient temperature sensor, an ambient pressure sensor, a temperature compensation sensor measuring the temperature of said mass flow sensor, and a control system is disclosed, as well as a method for measuring a flow using said flow regulating system, a device for the monitoring of air-borne compounds present in air in both a gas phase and a particle phase, wherein it comprises a sampling device, an enrichment trap 1, a calibration and tuning module, a blank module, said flow regulating system, a chromatography unit, and a detection unit, and a method for the detection of air-born compounds in an air flow by using said monitoring device.

39 Claims, 13 Drawing Sheets

(56) References Cited

U.S. PATENT DOCUMENTS

| | | | |
|---|---|---|---|
| 2002/0090309 A1* | 7/2002 | Yamashita | 417/423.4 |
| 2005/0109699 A1* | 5/2005 | Gerhardt et al. | 210/659 |
| 2007/0116083 A1 | 5/2007 | Oda et al. | |
| 2007/0174016 A1 | 7/2007 | Ding et al. | |
| 2010/0022990 A1* | 1/2010 | Karpowicz et al. | 604/543 |

* cited by examiner

US 9,329,066 B2

FLOW REGULATING SYSTEM AND MONITORING DEVICE COMPRISING SAID FLOW REGULATING SYSTEM FOR THE DETECTION OF AIR BORNE ANALYTES

FIELD OF THE INVENTION

The present invention relates to a flow regulating system for maintaining a stable air flow comprising at least one pump, a mass flow sensor, an ambient temperature sensor, an ambient pressure sensor, a temperature compensation sensor measuring the temperature of said mass flow sensor, and a control system, and to a method for measuring a air flow using said flow regulating system.

The present invention also relates to a monitoring device for the monitoring of air-borne compounds present in both gas phase and particle phase, wherein it comprises a sampling device, an enrichment trap, a calibration and tuning module, a blank module, said flow regulating system, a chromatography unit, and a detection unit, and to a method for said detection.

BACKGROUND OF THE INVENTION

There is a clear demand for the monitoring of air-borne compounds that can have health effects on exposed individuals. A great interest exists for compounds that have occupational exposure limit values, set by governmental bodies, to ensure that the levels of such compounds are satisfactory low. In many cases, it is not known what the air contaminants consist of and for this reason, it is of interest to learn more details about the nature of these "unknown" compounds and to reveal the identity of the most predominate ones. Another field of interest is to study and check the effect of measures with a view to reducing these levels in air, e.g. to check the "true" ventilation efficiency or other measures to control the air levels. Devices for this purpose can also be used for the monitoring of the quality of compressed air and air in respiratory protective devices. Other fields of application for such devices are e.g. the control of different volatile compounds present in food. Such compounds can be used as markers for degradation of certain food components or to monitor raw materials to ensure a satisfactory quality. Such devices may also be used to ensure that other compounds have not contaminated to food. In hospitals, such devices can be used to check the air levels of e.g. narcosis gases and to ensure that the personnel, patients or others are not exposed to toxic levels. Chemical warfare agents are compounds that need to be checked for in order to reveal the presence thereof and to ensure that individuals are not exposed.

In environmental analysis there is a need to monitor the quality of air in cities, public places and in the nature. One purpose is to obtain background data for statistical studies and to check if the levels are below the levels set by national and international bodies. They can also be used to check if the emission of industrial pollutants results in exposure in the nature or in populated areas. The achieved data can have an impact on decisions and interpretation of a certain situation. There is therefore a demand of a satisfactory high quality of the data.

There are many examples of air pollutants that occur in both gas and particle phase. Of special interest are the size fractions that have the ability to reach the lower respiratory tract. There are reasons to believe that the toxicology is different depending on not only the chemistry as such but also on the distribution on different target organs in the body of humans. There is a need to know more about the exposure to the respirable particle fraction present in air.

Numerous devices exist for the monitoring of air-borne compounds and there is a great variety of technology used. In principle, the devices can be grouped in selective and non-selective devices. Non-selective devices give a response for several compounds and do not differentiate between two or several compounds and may also result in false positive results. Such devices are today still used, possibly due to the low cost. In many applications, false positive results can give rise to a high cost for the user, if costly measures are performed from invalid data.

Selective devices give a certain response for a selected compound or a group of compounds. Other present compounds do not interfere with the result. The frequency of false positive results will be much less as compared to non-selective monitoring. The quality of the data obtained is essential. Typical factors that describe the quality of the data are: repeatability, reproducibility, linearity (calibration graph characteristics with intercept and background), detection limit and quantification limit. In addition, knowledge regarding the interference from other compounds is necessary. It needs to be mentioned that a certain compound can influence the result even if the compound does not itself give rise to a response.

Similar techniques for the detection of air-borne compounds involves the use of e.g. photo ionisation detectors (PID, Thermo Scientific, Franklin, Mass., USA), flame ionisation detectors (FID, Thermo Scientific, Franklin, Mass., USA), infrared detectors (IR), portable gas chromatography (GC)-PID (PID Analyzers, Pembroke Mass., USA), portable GC-mass spectrometers (MS, Inficon Inc., New York, USA), GC-DMS ((Differential Mobility Spectrometry), Sionex Inc., Bedford, Mass., USA). All techniques give a response for a certain analyte, but to know the concentration the response need to be translated to concentration by using information from a more or less sophisticated calibration curve. For many of the above techniques, the response varies with time due to ageing, contamination of the detector (reduces the signal) and other variables.

The GC-DMS technique mentioned above is used in the MicroAnalyser instrument (Sionex Inc., Bedford, Mass., USA). The GC-DMS technique is based on GC separation, with regards to compound volatility, in combination with the separation in a DMS sensor, with regards to other molecular properties such as size shape, charge etc.

There are several drawbacks with the present types of instruments. For PID and FID, identification of the individual chemicals is not possible. PID and FID detectors measure the sum of VOC (Volatile Organic Compounds). Infrared detectors suffer from problems with inferences. IR detectors are not possible to use when monitoring VOCs at low concentration when other interfering compounds are present.

For direct monitoring using GC-PID (e.g. VOC71M from Environment s.a.; www.environnementsa.com) and the GC-DMS instrument (e.g. Sionex Inc., Bedford, Mass., USA) there are limitations leading to inaccurate identification and quantification of analytes, and external complementary pre or post-calibration have to be made. For the existing products it is not possible to perform calibration automatically in the field. Further, there are problems with the occurrence of a non-linear relation between the sampling time and determined concentrations, which thereby disables long time sampling if the amount exceeds the calibration range. Further, when a volume is collected it needs to be calibrated to a volumetric volume and possibly corrected for the ambient temperature and air pressure. The sampling of a volume in a certain sampling volume container or on a sorbent followed by thermal desorption (in the case of a sorbent) and thereafter injecting the collected compounds on the GC the chromatographic peaks will be broadened in a way that the resolution of the chromatography will be affected.

Another problem in known techniques is analysing different analytes with a great difference in concentration. Compounds that have been introduced to the sampling system cause carry over problems and memory effects to samples that are analysed. In fact, there are no practical means to ensure that the estimated concentration is true if not a sample that represents the baseline or the background or the blank is analysed before and after the real sample from the environment is collected.

Another important parameter in this area is the gas flow containing the compound to detect, i.e. the analyte, in the apparatus used for the detection. During the sampling of compounds in air it is of importance to be able to control and log the flow and volume of the acquired amount of air through the sampling device as there is a direct correlation between the contents in a sample and the air volume collected. Taking several samples simultaneously is also of importance for three reasons, more precisely for increasing the accuracy of a certain sample, for detecting erroneous samples and for acquiring different compounds simultaneously. When handling sampling results, it is also important to be able to track how the sample was collected, the time, the flow, the temperature, the pressure and the humidity.

Existing solutions to maintain a stable flow during sampling do not prove to maintain a stable flow over time and requires field calibration. The flow speed needs to be calibrated before and after sampling to ensure that the sampling speed is correct and have not changed over time. A logging functionality is also often missing.

An existing solution tried is the SKC AirChek pump (see www.skcinc.com), where a differential pressure sensor indicates if a change in the flow system back pressure has occurred, and adjusts the pump control signal to compensate for this. However, this solution has proven to give drift errors over time, and a calibration with an external flow meter is required in order to set a certain flow rate of its pump.

Another existing solution is the Casella Apex pump system (see www.casellameasurement.com). It has a logging function, an ability to transfer logged data to a PC, and ability to control flow via a display and buttons. The inventors behind the present invention have conducted tests on these pumps in 2006, and the results did not concur with its specifications, as the pumps did not manage to keep a stable flow as a sampler inducing a certain backpressure was attached to it. For samplers with high backpressure, the Casella Apex did not work at all.

A problem with existing pump systems is that the flow sensors incorporated in them may fluctuate with the temperature of flow sensor electronics. Most flow sensors, using different techniques for the actual measurement of gas flow, have an output voltage signal corresponding to the measured flow. The output signal is however easily affected by the temperature of the electronic components in the flow sensor.

A further problem in existing apparatuses for the detection of air-borne compounds is the occurrence of a memory effect in the system in view of different analyte compounds and also other compounds of no interest to detect which have passed through the system. This phenomenon gives rise to inaccurate and erroneous detection results. The instrumentation is in most cases fully flexible and a tubing need to be connected from the measuring spot to the instrumentation. The tubing can in many cases be long and contains a certain volume. To get representative samples to be introduced into the instrument and the sampling device the volume needs to be flushed with several more volumes as compared to the volume of the tubings.

In view of this, there is a great demand for an improved direct monitoring device for the detection of air-borne compounds or analytes and for an improved method for the detection of such compounds or analytes.

There is further also a great demand for an improved pump for monitoring devices for the above mentioned detection of air-borne compounds, a pump that has the ability to deliver adequate pumping performance required for accurate measurements.

SUMMARY OF THE INVENTION

An object of the invention is to eliminate the above-mentioned problems and provide a device and a method for improved detection of airborne analytes at different locations of interest.

According to the present invention, this object is achieved by means of a monitoring device including a flow regulating system, a method for the detection of air-borne analytes as defined in the independent claims appended, and a method for measuring a flow using said flow regulating system. Useful embodiments are defined in the dependent claims.

According to one aspect the present invention relates to a flow regulating system for maintaining a stable air flow comprising at least one pump, at least one mass flow sensor, an ambient temperature sensor, an ambient pressure sensor, a temperature compensation sensor measuring the temperature of said mass flow sensor, and a control system. The input from the above mentioned sensors to the control system is adapted to regulate said at least one pump to keep a stable mass flow.

According to another aspect, the present invention relates to a monitoring device for the detection of air-borne compounds present in an air flow in both a gas phase and a particle phase, wherein it comprises a sampling device, an enrichment trap, a calibration and tuning module, a blank module, said air flow regulating system, a chromatography unit, and a detection unit.

According to a further aspect, the present invention relates to a method for the detection of air-borne analytes by use of the monitoring device according to the present invention, wherein it comprises the following consecutive steps;
  a) one or more different calibration and tuning modules containing different analyte references are inserted into the monitoring device,
  b) the air flow containing the air-borne analytes and a reagent is introduced in the sampling device to be reacted with each other therein,
  c) the sampling device containing the sampling tube, the filter and the sorbent, or the first sorbent, the filter, and the second sorbent, is heated with a view to releasing analytes adsorbed in the sampling device,
  d) the analytes released from said sampling device are collected in one or more enrichment traps,
  e) the analytes are subjected to a chromatography step,
  f) the analytes are detected quantitatively and qualitatively.

According to a still further aspect the present invention relates to a method for measuring a flow using said flow regulating system according to above. The method comprises the steps of:
  measuring the mass flow with the mass flow sensor,
  measuring the temperature of the mass flow sensor using said temperature compensation sensor, adjusting the mass flow measurement value according to a predetermined calibration of temperature related error and the measurement signal from said temperature compensation sensor, calculating a volumetric flow from said mass flow measurement using the measured mass flow, and the ambient temperature, the ambient pressure. The calculation of volumetric flow is performed by utilizing said measured values of mass flow, ambient temperature, and ambient pressure and the ideal gas law.

The back pressure sensor enables real-time monitoring of how air sampling is proceeding and is logged to present information of quality of sampling. Further, the back pressure sensor and/or the mass flow sensor enable monitoring of flow pulsation characteristics. From this the flow pulsation can be reduced by introducing a device inducing a cancellation pulse.

The flow regulating system can be stacked or be part of a cluster of flow regulating systems for validating the collection of air samples. With several flow regulating systems stacked simultaneous sample collection can be performed. When two of said flow regulating systems are used simultaneously, where one of said systems have e.g. half the flow rate of the other, the breakthrough or overloading of samples can be evaluated.

SHORT DESCRIPTION OF THE DRAWINGS

DETAILED DESCRIPTION OF DIFFERENT EMBODIMENTS OF THE INVENTION

The present inventors have eliminated or reduced the problems mentioned above in connection with known techniques in the area of detection of air-borne compounds in different environments by the provision of the monitoring device and the method for the detection of air-borne analytes according to the present invention.

The analytes of interest to detect are in general:

Solvents: 1,2,3-trimethylbenzene, 1,2,4-trimethylbenzene, 1,3,5-trimethylbenzene, 1-Butanol, 1-Butanone, 2-methylnaphthalene, 4-methylbenzaldehyde, Acetone, Acetonitrile, Acetophenone, Acetaldehyde, Acetylene, Benzaldehyde, Benzene, Bromomethane, COS (Carbonyl Sulfide), Cyanuric Acid, Cyanogen Chloride, Cyclohexane, Decane, Dichloromethane, Dimethyl ether, DIMP, DMMP, DPM, Ethanol, Ethyl Acetate, Ethylbenzene, Eucalyptol, Fluroethane1112/Freon 134a, Freon 22 CFFM, Freon152a, Hexadecane, Hexanal, Hexane, Hydrochloric acid, Isobutylene, Isopropanol, m xylene, Methanol, Methyl acetate, Methylcyclohexane, MES (Methyl Ethyl Sulfide), Methyl Salicylate, Naphthalene, Nitric Dioxide, Nonanal, oxylene, Octamethylcyclotetrasiloxane, Octane, p xylene, Pentamethyl-diethylenetriamine, Pentane, Styrene, Sulfur Dioxide, TBM (tert-Butyl Mercaptan), Tetralin, tetra Hydro Thiophene, Toluene, Tridecane. Tris(1-chloro-2-propyl) phosphate, Urea, and compounds containing functional groups such as: isocyanates, isothiocyanates, amines, aldehydes, ketones, ethers, esters, phenolics etc.

Explosives: AN, DNT, EGDN, TATP, o-MNT, DMNB, p-MNT, NG, HMTD, RDX/C4, TNT, PETN, Tetryl Chemical Warfare Agents: VX, GA (Tabun), GB (Sarin), GD (Soman), GF (Cyclosarin), HD (Sulfur Mustard), L (Lewisite), HN3 (Nitrogen Mustard), AC (Hydrogen Cyanide), CK (Cyanogen Chloride), but in principle any compound present in an air flow is possible to detect by use of the present invention, provided that it can be trapped in the sampler. The term "analyte" used throughout the application text is intended to mean the specific compound or group of compounds to be detected in the analysed air flow. The term "sample compound" or "analyte compound" could also be used as a synonym.

The present invention is useful within military, the petroleum industry, chemical industry, oil industry, plastics industry, airline industry, food industry, cosmetics industry, respiratory protective device industry, related to environmental analysis, work environmental analysis, quality control and as alarm instrument, in particular within the environmental and work environmental applications, but it is in principle useful within any area in which air-borne compounds which are unhealthy or disadvantageous of any other reason are suspected to be present.

Figure 1:
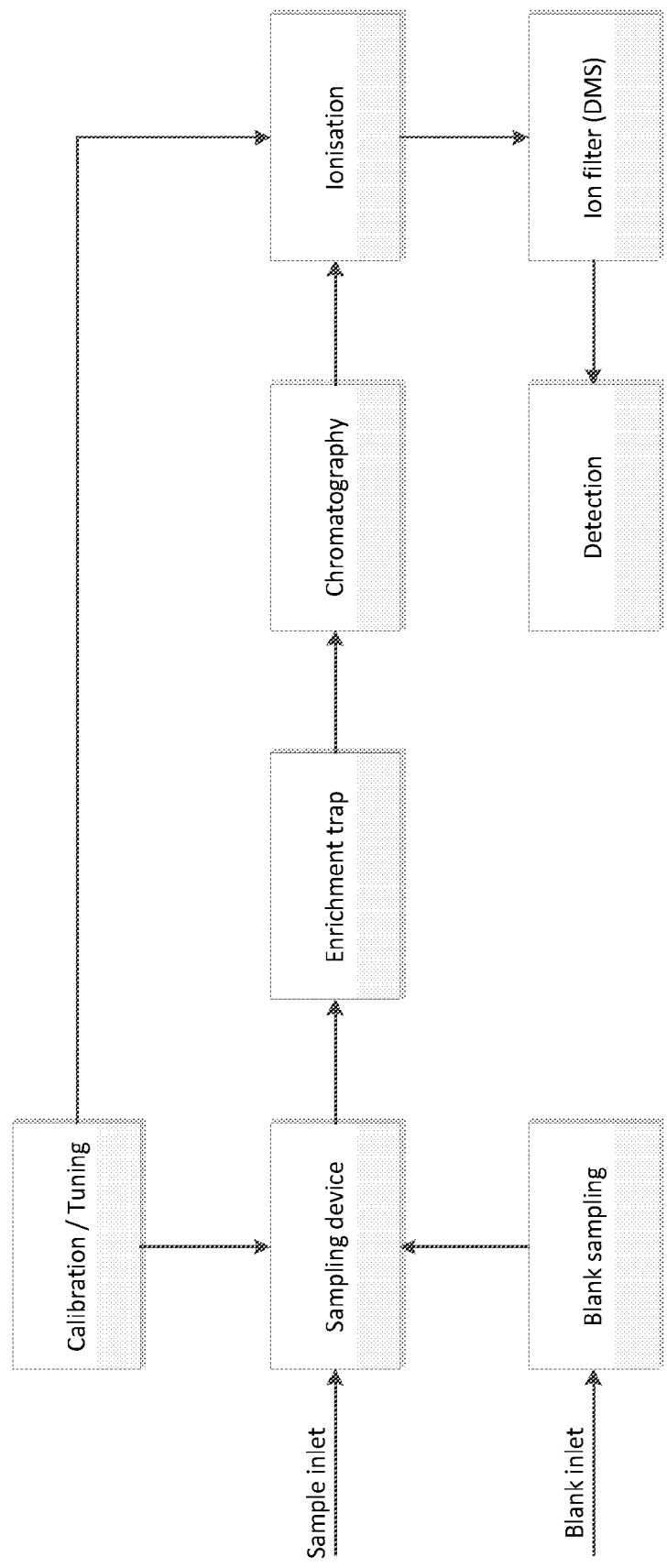
FIG. 1 shows a flow chart of one embodiment of the method according to the present invention.

FIG. 1 shows schematically one embodiment of the method according to the present invention. An air sample is introduced via the sample inlet into a sampling device. A blank is also introduced into the sampling device via a blank inlet. The analytes are collected in the sampling device and are then subjected to thermal desorption, wherein they emit the sampling device and are transported to an enrichment trap. After a further thermal desorption step the analytes emitted from the enrichment trap and are then chromatographically separated. Then the analytes are ionized and passed through an ion filter, followed by a qualitative and quantitative detection step.

An inlet need to be present that delivers the air or atmosphere to the sampling device. The inlet should deliver a defined air flow from the sampling atmosphere through the sampling device. The inlet may be a heated capillary that minimise the surface interaction between the capillary walls and the analyte during the transport of the air to be analysed to the sampling device. Optionally, the inlet may be provided with a tubular device attached to the inlet opening with a view to facilitating sampling in areas where it is difficult to arrange the monitoring device at a location where a reliable measurement of the air flow is obtainable, e.g. when the air flow is at a distance from the monitoring device. One or several tubing or transfer lines can be attached to the instrument or the sampling device.

The monitoring device according to the present invention comprises a sampling device for sampling of the analytes in the air flow introduced into the monitoring device. An efficient and controlled sampling of both gas and particles in the air flow is required. The sampling device according to the present invention has the ability to differentiate between the analyte present in the gas phase and/or in the particle phase of the air flow. A similar sampling device (EasySampler) having this differentiating ability is disclosed in WO 00/75622 and in US-2006-0239857 (Gunnar Skarping & Marianne Dalene). With reference to FIGS. 2-5 four different embodiments involving the sampling device will be disclosed below.

Figure 2:
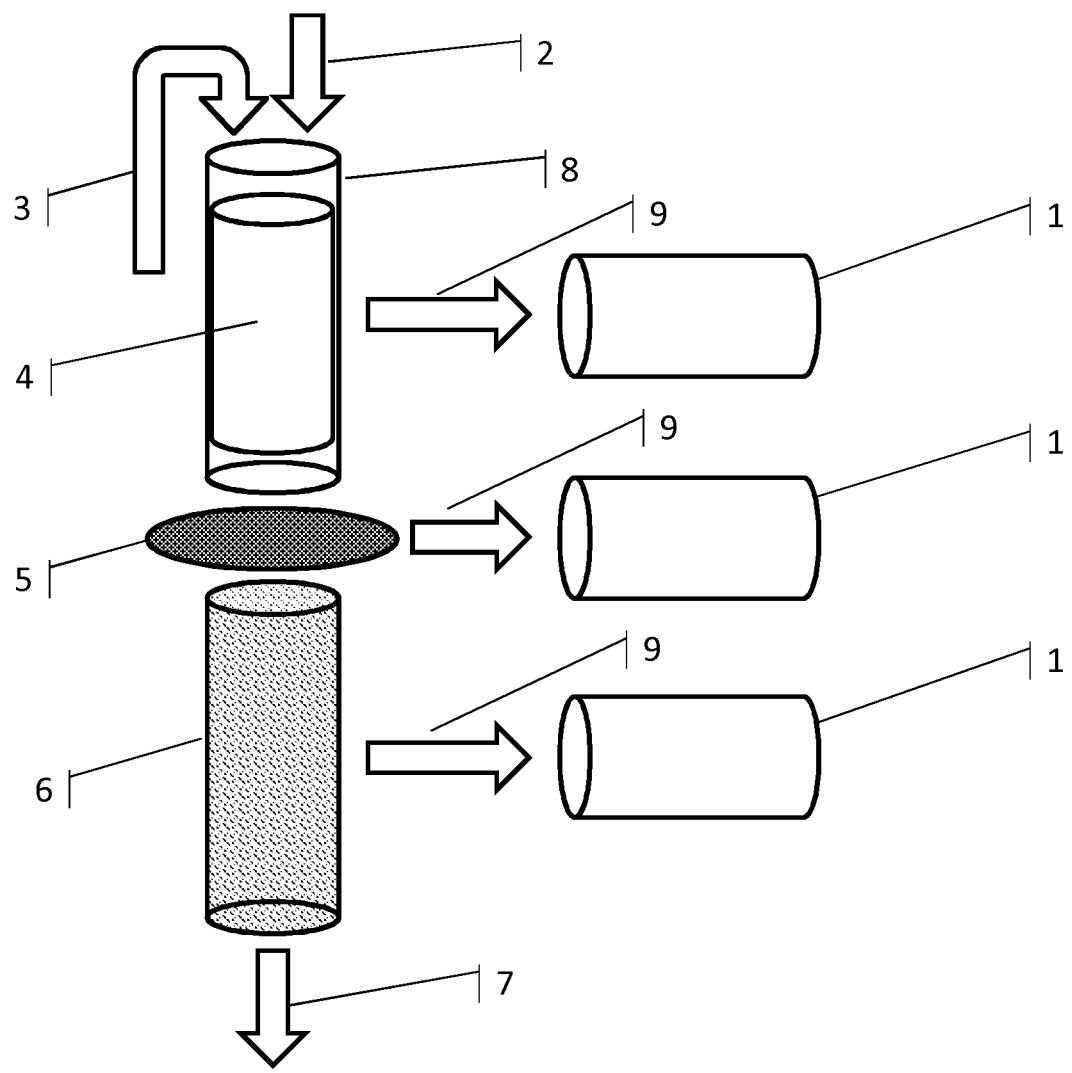
FIGS. 2-5 show four different embodiments of the sampling tube connected to one or more enrichment traps in the monitoring device according to the present invention.

In a first embodiment a sampling tube 8, also called denuder, is used for collection of the analytes in the gas phase of an air flow 2 introduced in the inlet of the monitoring device, and a filter 5 is used for the collection of the analytes in the particle phase of said air flow 2. As appears from FIG. 2, the filter 5 is arranged below and connected to the sampling tube 8 in such a way that the air flow 2 first passes through the sampling tube 8 and then continues through the filter 5. Simultaneously with the introduction of the air flow 2 to analyse a flow of a reagent 3 is pushed via a separate inlet into and through the sampling device. During the sampling step the analytes in the gas phase of the air flow 2 are absorbed on the wall of the sampling tube 8 and are there reacted with the reagent introduced. The sampling device may also contain a carrier 4 for the collection of the gas phase analytes. Said reagent is a volatile compound that reacts with the reactive analyte and protect it from further degradation. The reaction product will then be thermally desorbed and analysed. E.g., if the analytes are isocyanates, the reagent is DBA (di-n-butylamine) or another kind of secondary amine. Particles carrying analytes are not collected in the sampling tube 8. Instead, the analytes on the particles which have passed the sampling tube 8 and reach the filter 5 react with the reagent present therein and are collected on said filter 5. Said particles are then trapped on the filter 5. An absorbent 6 is arranged below and is connected to the filter 5 for collection of gas phase analytes that have been emitted from the particles trapped on the filter 5. After the sampling step (10 seconds up to several hours) a step of thermal desorption of the different parts of the sampling device (sampling tube 8, filter 5, absorbent 6) is performed (50-400° C., 10 seconds to hours, heated with electrical resistance heater or peltier element or microwave heating), wherein the analytes are released from each of said parts of the sampling device. In order to determine the analyte concentration or gas and particle concentration separately, the thermal desorption according to a first embodiment is performed for the sampling tube 8, the filter 5 and the sorbent 6 separately, as is shown in FIG. 2. The analytes emitted from the different parts of the sampling devices during the thermal desorption step are transported through exits from each of said parts of the sampling device via a tubing/conduit/pipe 9 and are then trapped on a focusing trap 1, respectively, as shown in FIG. 2.

Figure 3:
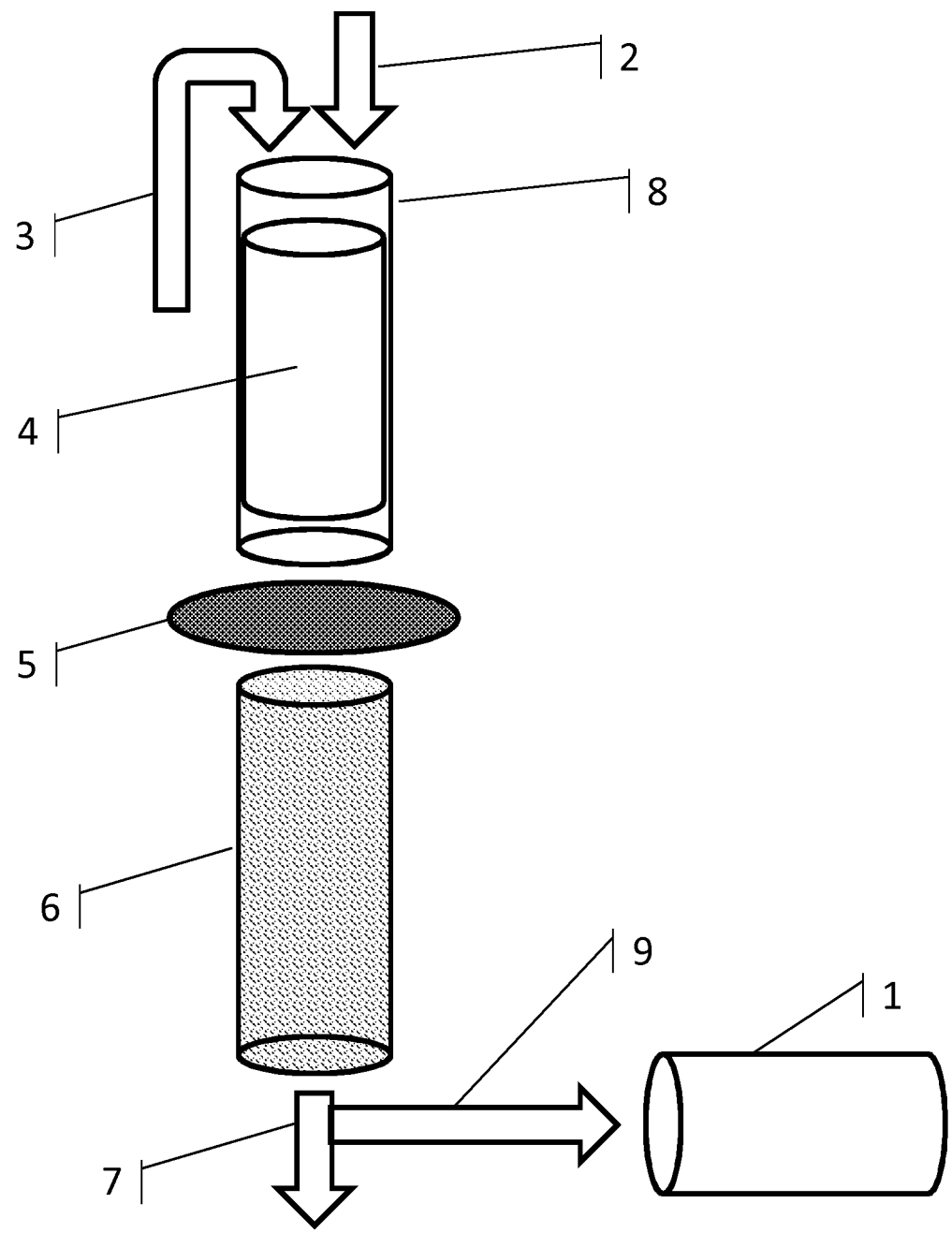

In order to determine the total analyte concentration the thermal desorption is, according to a second embodiment, performed for the whole sampling device, and the analytes released from the different parts of the sampling device are transported via an outlet 7 in the bottom of the sorbent 6 to an enrichment trap 1 via a conduit 9, as shown in FIG. 3.

Figure 4:
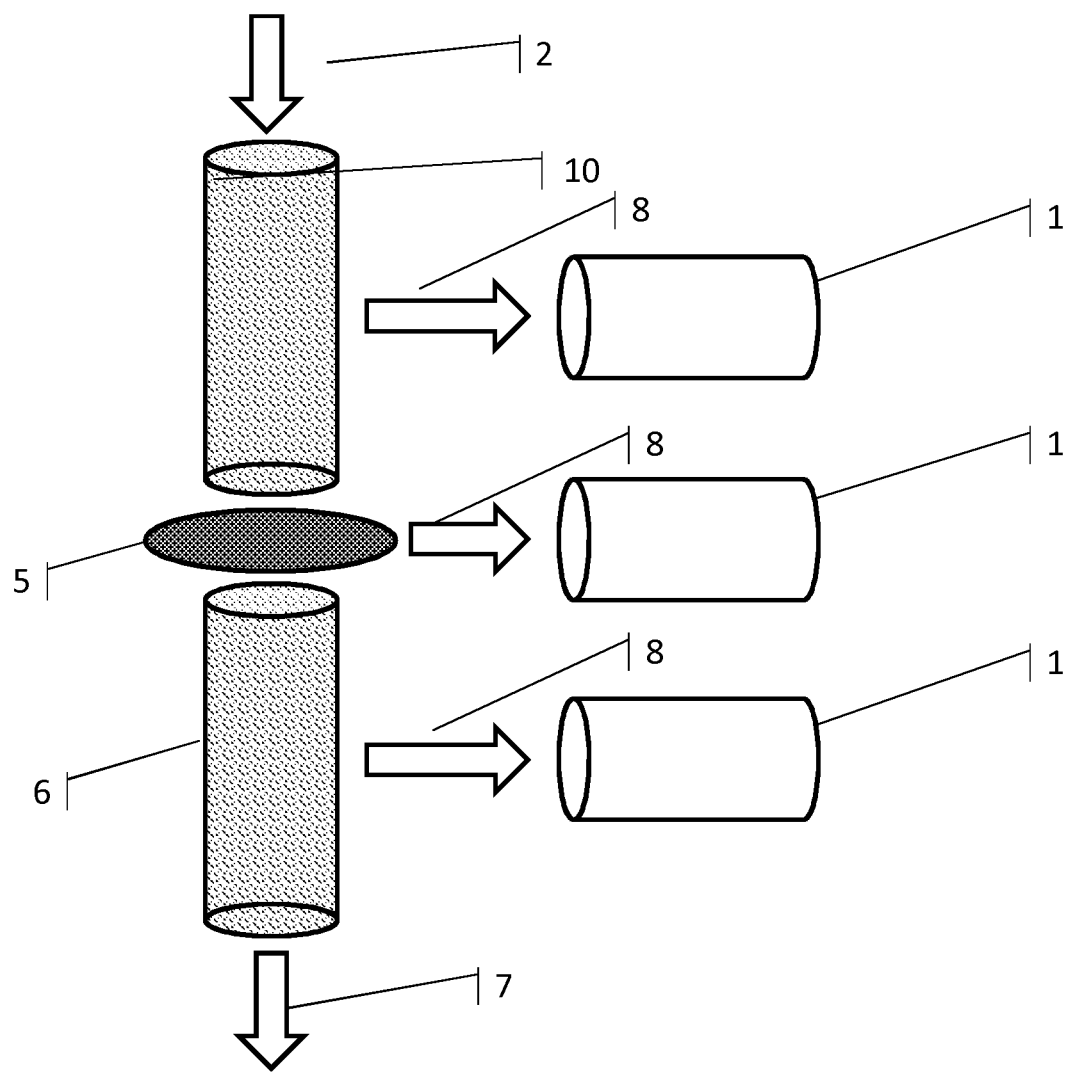

According to a third embodiment shown in FIG. 4, a tubular sorbent 10 is used instead of the sampling device 8 for collection of the analytes in the gas phase of the air flow 2. Thus, the sampling device in this third embodiment comprises both a first sorbent 10 and a second sorbent 6. Otherwise, the action of the sampling device according to said third embodiment corresponds to that according to the first embodiment. Further, according to a fourth embodiment shown in FIG. 5, the total analyte concentration in the whole sampling device may be determined in a way corresponding to that disclosed in the second embodiment.

FIGS. 2 and 3 show the sampling of reactive compounds (e.g. iso-cyanates) that are derivatised into stable derivatives. After sampling the analytes are thermally desorbed and transferred to the enrichment trap. After trapping on the enrichment trap the compounds are thermally desorbed and injected to the chromatographic column. In FIG. 3 the analytes in the different sampler parts 8, 5 and 6 are analysed together and the sum of all analytes are analysed in one chromatographic run. In FIG. 2 the analytes in the different sampler parts 8, 5 and 6 are analysed separately. Information is achieved regarding the analyte in gas phase and in particle phase. In addition, data is achieved regarding analytes that have evaded the samples in the filter 5 by analysing the sorbent 6.

Figure 5:
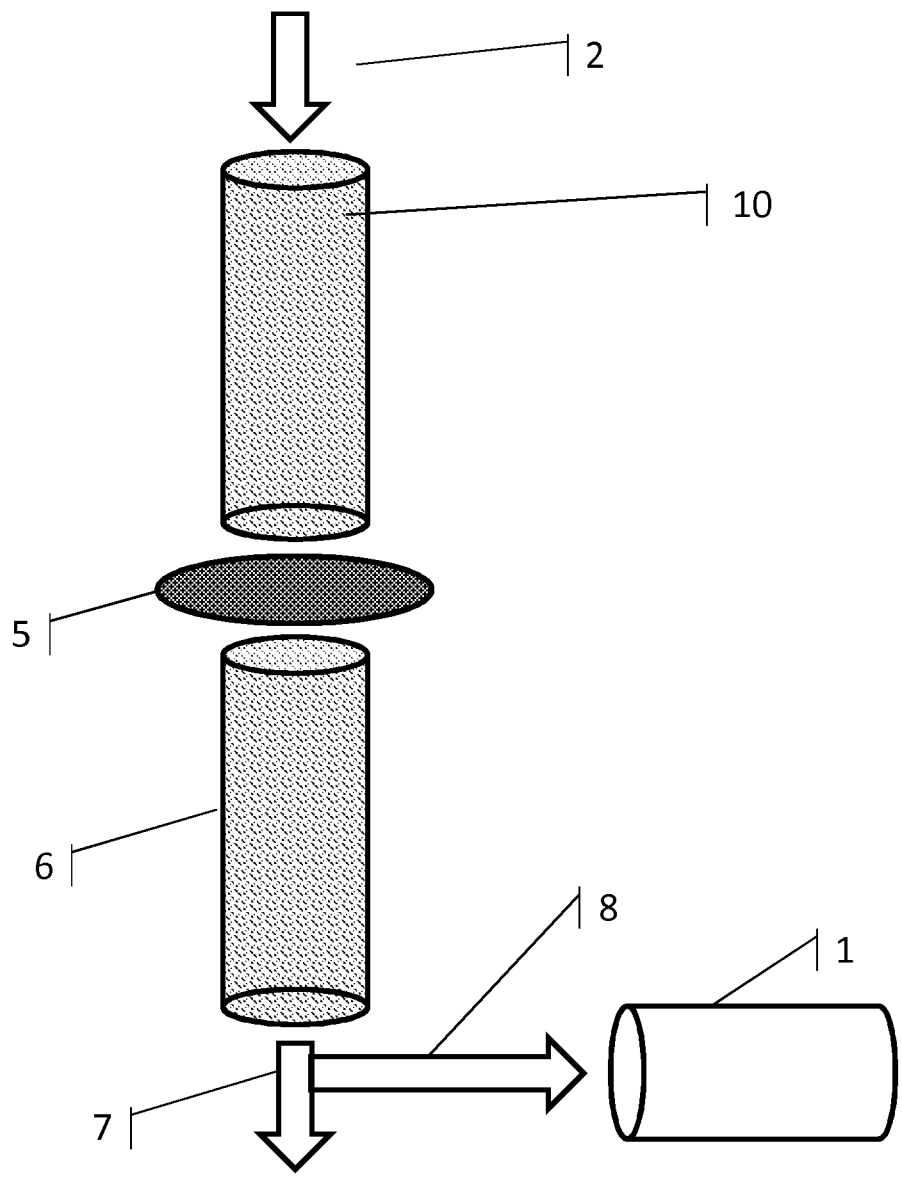

In FIGS. 4 and 5 the sampling is demonstrated for unreactive compounds such as benzene, toluene etc. After sampling the analytes are thermally desorbed and transferred to the enrichment trap. After trapping on the enrichment trap the compounds are thermally desorbed and injected to the chromatographic column. In FIG. 5 the analytes in the different sampler parts 8, 5 and 6 are analysed together and the sum of all analytes are analysed in one chromatographic run. In FIG. 5 the analytes in the different sampler parts 8, 5 and 6 are analysed separately. Information is achieved regarding the analyte in gas phase and in particle phase. In addition, data is achieved regarding analytes that have evaded the samples in the filter 5 by analysing the sorbent 6.

Figure 6A:
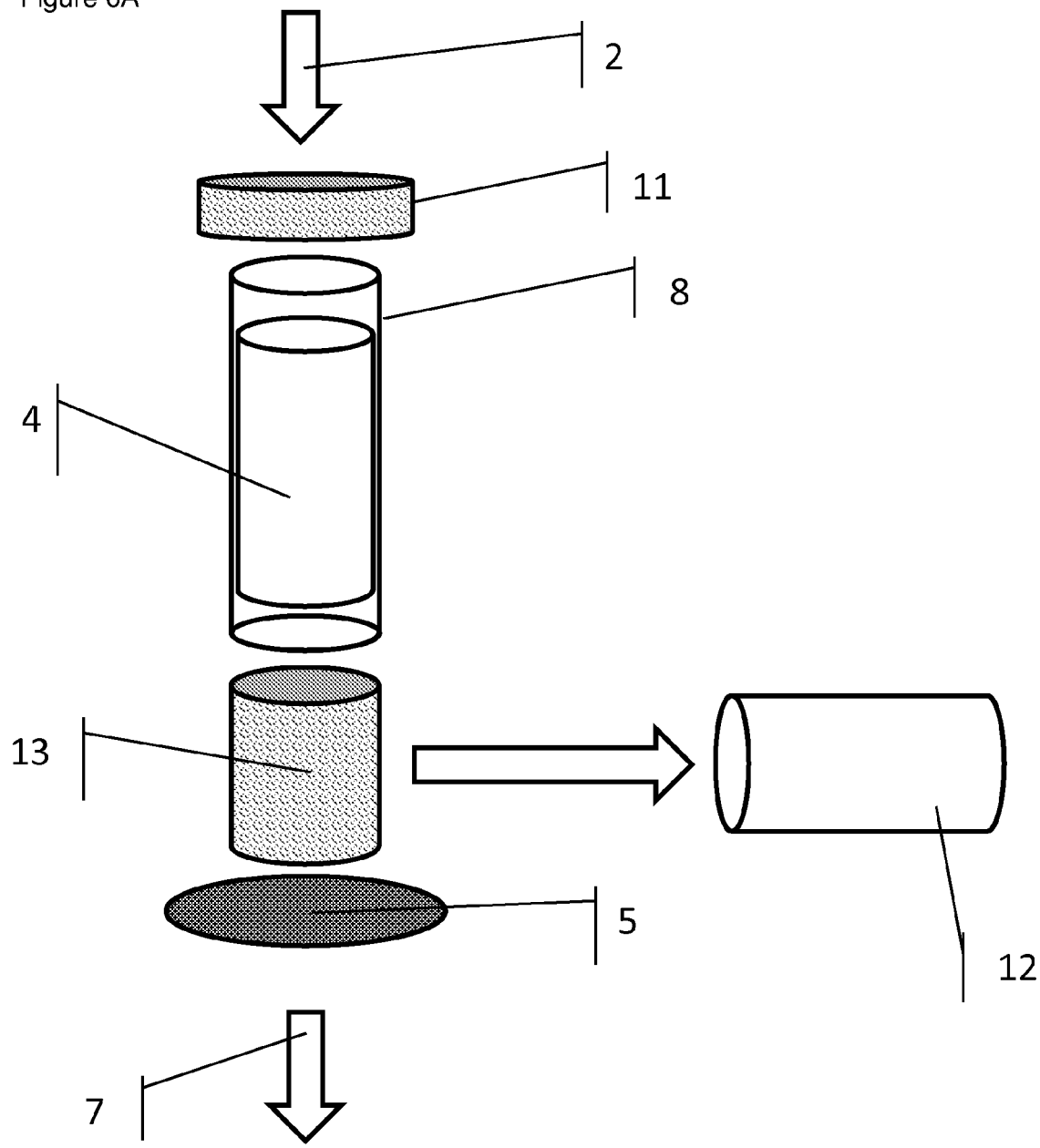
FIG. 6A shows one embodiments of a particle size selective sampling device according to the present invention.
Figure 6B:
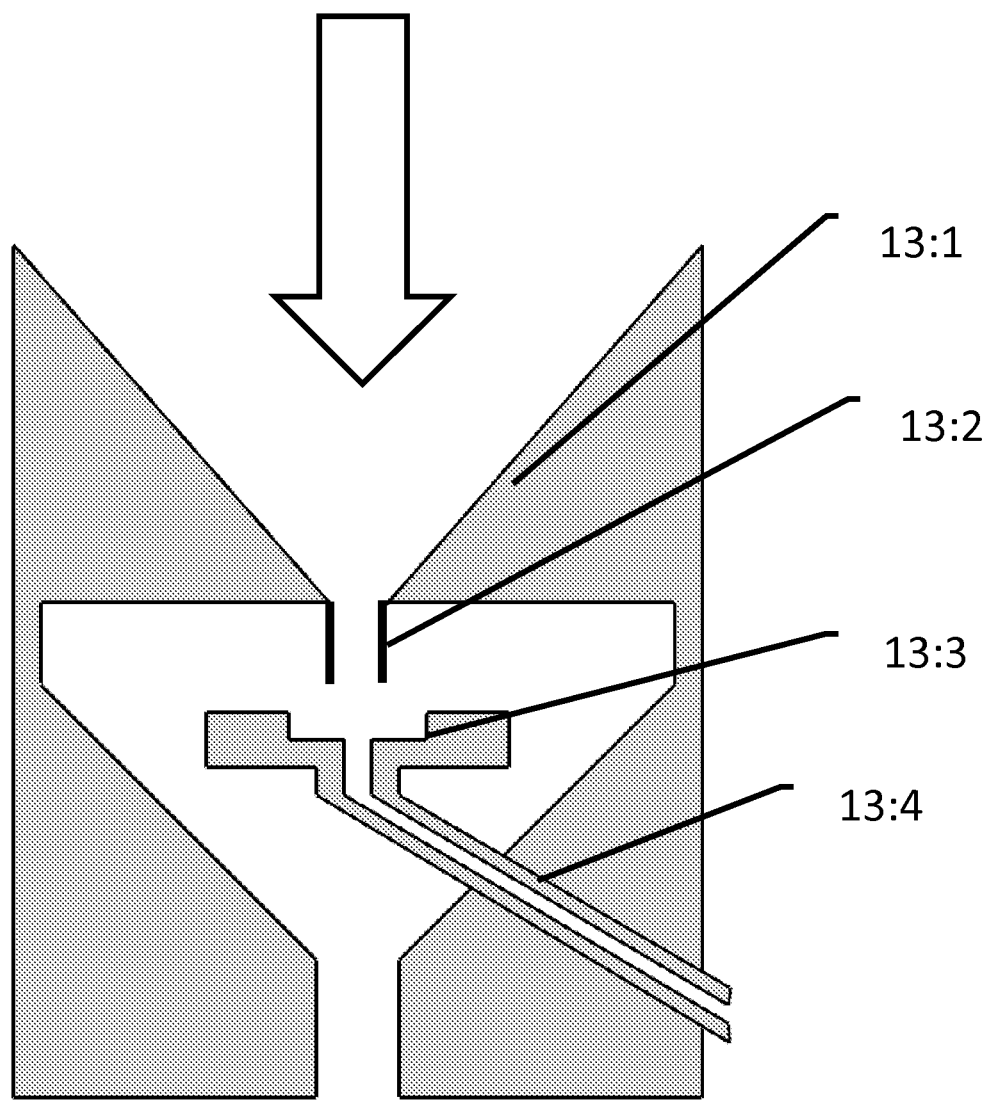
FIG. 6B shows in detail the impactor 13 of the sampling device shown in FIG. 6A.

In FIG. 6A an example of a particle size selective sampling device according to the present invention for air-borne compounds is presented. A pre-selector 11 is arranged in the inlet of the sampling device with a view to removing large particles, typically having a diameter larger than 100 nm. The pre-selector 11 has the purpose to remove the large particles preventing them from entering the denuder 8 (sampling tube) of the sampling device. The flow direction in the pre-selector 11 is changed and the large particles will deposit in the pre-selector 11. A carrier 4 in the denuder 8 collects the gas phase compounds. For e.g. isocyanates, the denuder 8 is covered on the inside with a glass filter coated with a mixture of acetic acid and di-n-butylamine (DBA). Isocyanates are efficiently reacted with DBA to stable urea derivatives and are trapped in the denuder 8. In series there is arranged an impactor plate 13 with a view to separating (cutting off) particles larger than inhalable (<100 nm) or respirable (<4 µm) sizes. The separated particles passing the tube 13:4 are collected in a filter 12. As shown in FIG. 6B, the flow passes through a cone 13:1 with a small nozzle 13.2 to speed up the linear flow. The flow stream is directed to an impactor plate 13:3 to trap said particles. The impactor plate 13:3 can be a small plate where particles impact and are deposited and retained. Alternatively, the impactor plate 13:3 is connected with a tube 13:4 having a small flow, about ⅕-¹⁄₁₀₀₀ or typically ¹⁄₁₀ of the main flow, to separate the particles larger than the cut off size from the main flow stream. Further in series there is a filter 5 arranged to collect inhalable or respirable particles. Such respirable or inhalable particles are efficiently collected on said filter 5 (e.g. 0.4 µm). In one embodiment said filter 5 is impregnated with DBA-acetic acid. During sampling the filter 5 is flushed with DBA that is evaporated from the denuder 8. Efficient derivatisation of the isocyanates is thereby made possible.

The impactor 13 is here described for isocyanates. It can also be used for other air-borne organic and inorganic compounds that are particle borne. Further it can be modified to separate other size fractions of <100 µm. The particle size selective sampling device is here described as a stand-alone sampler but it can also be an integrated part of a direct reading instrumentation.

The present particle size selective sampling device is useful as the sampling device in the monitoring device according to the present invention. Further, as said particle size selective sampling device per se not is known before, the present invention also relates to it per se.

The monitoring device according to the present invention also comprises a calibration and tuning module, which is attachable and detachable from the monitoring device. Said calibration and tuning module may be present in a cassette containing one or more different reference compounds in view of the analytes to detect. When desired, this module may be replaced with a new module with the same or other reference compounds.

It is well-known that all electronic monitoring devices needs to be calibrated at the factory, and in the field the calibration needs to be validated. The monitoring devices in the known techniques lack a calibration function or require complicated or costly calibration measures, e.g. the above-mentioned GC-DMS instrument from Sionex. The calibration is performed by analysing blanks and reference standards at different concentration levels.

The calibration and tuning device according to the present invention requires little user intervention. During the calibration mode, the computer connected to the calibration and tuning device manages flow valves, timings and data analysis automatically. In the few steps where user interaction is required, the user will be guided via a graphical user-friendly interface, explaining every step. An advanced calibration mode where the user has full control over the calibration parameters is also available. Together with the factory calibration, continuos tunings and calibrations will ensure that calibration data will be available to convert non-linear data to a linear result as long as the relation between the non-linear data and the result is strictly monotone within the relevant interval. This conversion will take place in the software of the computer involved.

During the calibration step a defined concentration and a defined volume mass of a relevant calibration compound is delivered from the calibration and tuning module to the sampling device, and this is performed several times in order to check for any drift.

Figure 7:
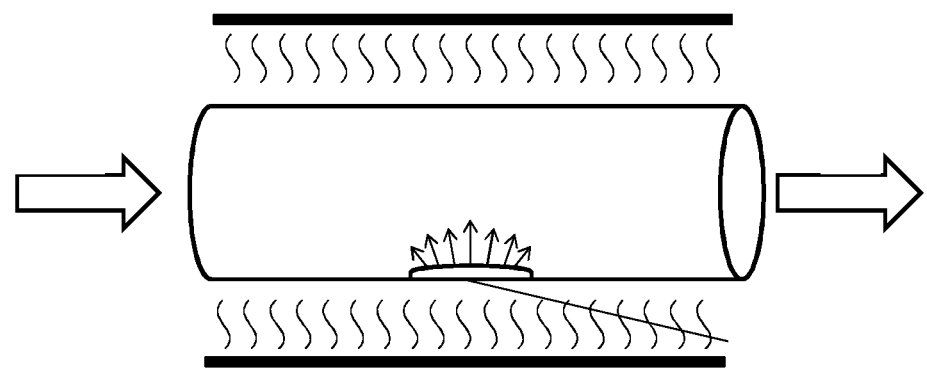
FIG. 7 shows one embodiment of the calibration and tuning device in the monitoring device according to the present invention.

Referring to FIG. 7, which shows a part of one embodiment of the calibration and tuning module, said module contains a closed unit, preferably a cylindric or tubular unit, e.g. a permeation tube that is typically made of silicone, teflon or a another type of inert permeable polymer, containing one or more reference compounds in gaseous form or in the form of a liquid or a solution. Said unit has an inlet and an outlet and is surrounded, preferably concentrically, by a heating device, and during heating of said unit said one or more reference compounds are released at a defined rate and penetrates through the walls of the closed unit.

To electronically identify the closed unit of the calibration and tuning module there are several solutions. One solution is to have an integrated circuit containing logic that can provide a unique ID for the container. It can also be a number of electrical resistances, over which a voltage is measured when connected to the main controller. A series of voltages gives the module an unique fingerprint. For quantitative calibration the calibration module is characterised by its ability to deliver a certain amount of the compound per time unit. By varying the temperature the amount per time unit released is affected. When introduced to the enrichment trap the amount that is trapped is dependent on the time and the temperature of the calibration device.

The expression "calibration and tuning module" used throughout the present application means that said module at the same time has the ability to calibrate, for quantitative measurements the monitoring device with reference compounds and to tune the monitoring device against specific analytes at a measurement location, wherein the monitoring device recognizes the specific analyte and focuses and adjust the detection parameters in such a way that the measurement of said specific analyte becomes more exact and reliable than otherwise. Said tuning is regulated by a computer.

More precisely, detector parameters, e.g. for DMS equipment, such as the RF voltage and the compensation voltage, needs to be optimised. Also the retention time on a GC column needs to be optimised. The tuning is performed by introducing reference standards to the sampling device or direct to the detection unit, e.g. the DMS sensor.

The software controlling the tuning in the computer may have a prediction about the result for the specific compound in question. The prediction can be made from factory calibration or from previous tunings. When the sampling of the tuning module is made, the prediction will be tuned to a new calibration by the sampling result.

The present invention relates to a flow regulating system as defined in claim 1 as well as to a monitoring device comprising said flow regulating system. Said air flow regulating system comprises, inter alia, a computer regulating the pump, a mass flow sensor for the gas to be analysed, a temperature sensor, and a pressure sensor, wherein the input from said sensors and any further sensors to said computer regulates said at least one pump to keep a stable mass flow. This has so far not been possible with known instruments and apparatuses used in the art.

A stable, defined volumetric gas flow reduces errors derived from the flow rate. This could, according to the present invention, also be accomplished by a conventional flow regulating system that is different from the flow regulating system defined in claim 1, as long as an acceptable flow is maintained in the monitoring device during analysis. According to one aspect of the present invention a stable, defined volumetric gas flow is, however, accomplished by said flow regulating system controlled by a computer. The computer acquires signals from several sensors, e.g. a mass flow sensor, an ambient temperature sensor, an ambient pressure sensor, a flow system back pressure sensor and a temperature sensor that measures the flow sensor's temperature and compensates its non-linear behaviour over temperature. With data from these sensors, the computer regulates the pump to keep a stable flow as close as possible to the desired flow. Flows, temperatures, pressures, humidity, for the flow system are all logged.

The present inventors have created a solution to the above-mentioned problems in connection with unstable air and gas flows. The aim of the inventors was to find a solution wherein a gas flow through a sampling device can be set to a desired flow rate, whereas a control system measures and controls the flow to keep it stable at the desired rate and logs the flow in order to ensure proper sampling and to track how the sampling was made. The solution should also include a way to conduct several samplings simultaneously. The flow measurements should be robust with respect to several degrees of freedom: temperature and pressure span within relevant atmospheric conditions (to make a proper volumetric flow conversion) and backpressure levels for existing "heavy" samples (up to 15 kPa). The solution should also make it possible to transfer logged data of flow, time, temperature and pressure to a PC, and to set up a device to make a proper sampling acquisition. Via a wireless connection, one pump servers as master, other pumps as slaves, and a network of pumps may be controlled from the master pump, or from a PC serving as master.

Figure 8A:
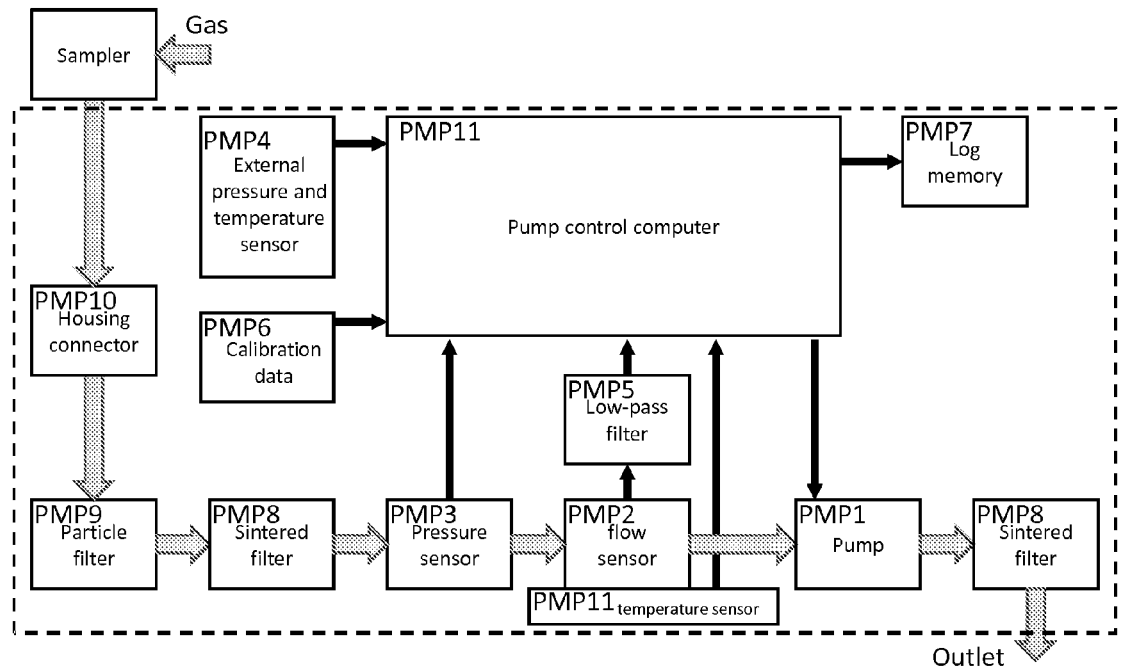
FIGS. 8A and 8B show in detail one embodiment of the gas flow regulating system and the computer regulated pump in the monitoring device according to the present invention.

A schematic flow chart of the components inside the gas flow regulating system according to one aspect of the present invention is shown in FIG. 8A. The gas flow regulating system of FIG. 8A is located after the sampling device in FIG. 1

The pump (PMP1) is controlled to keep a stable flow at a user defined setpoint, which is compared to a correct flow measurement. This measurement is made via a mass flow sensor and several compensation steps described in section "Flow measurement system" below.

The gas flow is induced by a four baffle rotary vane pump PMP1). The gas flow could be induced by any electrical gas pump, or any device being able to be controlled electronically and being able to induce a flow. The flow is measured by a mass flow sensor (PMP2) whose signal is compensated for the non-ideal properties of mass flow sensors with respect to temperature and pressure. The flow measurement procedure is described more in detail in section "Flow measurement system" below. Dust and other particles may contaminate the sensitive flow sensor. A particle filter (PMP9) prevents contamination of the flow system. For IECEx (International Electrotechnical Commision, Explosive atmospheres) and ATEX (EU directive 94/9/EC: Appareils destinés à être utilises en ATmosphères EXplosibles) considerations (spark mitigation), sintered filters (PMP8) will also be included in the flow system.

The flow system is able to maintain a stable flow not deviating more than 2% from the desired flow, which may be set in the range 1 ml/min to 4000 ml/min.

Flow Regulating System

Figure 8B:
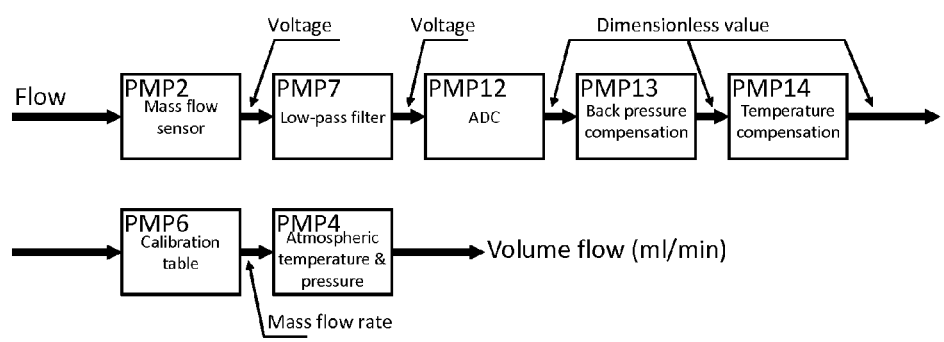

The control system relies on that the flow can be measured accurately. In order to acquire a correct measurement of the flow, the steps shown in FIG. 8B are taken.

Each step is crucial for acquiring a correct flow measurement. Each step's solution and alternatives are described below.

The main sensor for controlling the flow is a differential mass flow sensor (PMP2). The principle of this sensor is that the gas flows through a passage in this sensor, in which a heating element is situated. Before and after the heating element, a differential temperature sensor is situated. The gas is heated when passing the heating element. The temperature difference before and after the heating element corresponds to a certain flow rate. The output signal of the mass flow sensor is a voltage between 1V and 5V. Other mass flow sensors that can be miniaturized could also be used, e.g. a coriolis mass flow sensor.

The output signal of the mass flow sensor contains noise, mainly derived to the non-laminar flow pumps induces. The output signal is filtered by an electronic active low-pass filter (PMP7) with a cut-off frequency at 5 Hz.

The low-pass filter could also be implemented as
a) a passive low-pass filter, with resistances, inductors and capacitors,
b) a software algorithm, either by averaging or using a fast fourier transformation, or
c) a flow pulse filter, reducing the pulses in the flow, making the initial flow sensor signal less noisy.

The voltage is converted to a digital value using a 14-bit ADC (Analog-to-Digital Converter (PMP12)). The ADC uses successive approximation. It could have any resolution larger than 10 bits, and it could be of $\Sigma\Delta$-type or integrating type. The mass flow sensor is not ideal for all conditions, and may be subjected to drift with increasing back pressure. Therefore a backpressure sensor (PMP13) is introduced for making it usable for relevant backpressures (0-15 kPa). The backpressure sensor is a differential pressure sensor measuring the difference between atmospheric pressure and the pressure inside the flow system. This value is used in a compensation algorithm in software. The backpressure measurement could be measured by:
a) having an absolute pressure sensor inside the flow system and comparing the reading with the absolute atmospheric pressure sensor, or
b) having an absolute pressure sensor inside the flow system and using a differential pressure sensor for reading the atmospheric pressure.

The mass flow sensor signal drifts with its temperature. Therefore, the temperature of the mass flow sensor must be measured in order to acquire a correct flow for different ambient temperatures. Attaching a temperature compensation sensor (PMP14) to the mass flow sensor body makes it possible to compensate the temperature drift of the mass flow sensor. The relation between the mass flow sensor voltage signal and the actual flow is not linear, and differs between flow sensor individuals. Therefore a factory calibration data table (PMP6) is established to convert the mass flow signal to a mass flow. The calibration data table contains a number of posts with signal values and corresponding mass flow. When converting a value to a flow, an interpolation is made between the closest values in the calibration table.

The calibration data table could be replaced with a polynomial function describing the relation between mass flow and sensor signal.

In order to convert the mass flow figure to a volume flow, the ideal gas law is applied, wherein the atmospheric pressure and temperature is measured by a atmospheric conditions compensation sensor (PMP4). This measurement could be made by separate sensors for temperature and pressure. The pressure measurement could be made using an absolute pressure sensor inside the flow system and a differential pressure sensor between flow system and atmosphere.

The flow control or regulation is implemented as an application running on a microcontroller computer module. It could also run on an embedded PC. The control system needs a correct measurement of the flow, as is described in section "Flow measurement system" above. The flow measurement is compared with the desired flow set by the user. This comparison is made in a software PID controller. The PID controller controls the output signal to the pump.

A fuzzy logic part in the software evaluates the control signals needed to the pump for maintaining a certain flow given a certain back pressure. From these data, the fuzzy logic part can override the PID controller when a condition in the flow system is drastically changed (back pressure, desired flow) in order to achieve a faster response. The pump inducing the flow is controlled by a Pulse Width Modulated signal. It could also be controlled by the output voltage from a D/A converter.

Mechanical parts in the flow system will be worn over time. Diagnostics for the flow system will be implemented by comparing the following three properties: flow system back pressure, pump control signal and flow measured by the mass flow sensor. By comparing data from the internal pressure sensor (PMP3), the mass flow sensor (PMP2, and the signal level to the pump (PMP1), diagnostics of the flow system can be achieved. The diagnostics software has several assumptions, e.g. "if the pump needs a high control signal even though neither back pressure nor flow measured is high, the pump is in a bad condition".

The measured flow is logged on a digital (flash) memory (PMP7). Additional parameters logged are temperature, pressure, humidity, GPS position, and time. The log files can be administered on a computer with USB. The pump can be connected to a PC via USB. In order to control several pumps simultaneously, they need to be connected to each other. A pump can be connected to a PC or other pumps via Bluetooth. Other wireless connections can be implemented (i.e. ZigBee, WiFi).

The pump contains one or several Li-ion batteries. The batteries may either be charged via USB connection to a computer or via a USB-wall adapter. A battery indicator will be available for displaying battery level for the user. The battery indicator may be implemented as one or several LED(s) or integrated in a graphical user interface. The operating time of the pump is estimated to 12 hours for standard sampling conditions. The device is equipped with an OLED display displaying current flow.

The display can be omitted or replaced by a 7-segment display, graphical LCD, matrix character LCD (e.g. HD4470), LEDs, indicating proper flow, and E-paper display. The user controls the pump via several buttons, that have different purposes depending in which menu state the user interface is in. An example is two buttons, where one steps through the graphical menu alternatives, and the other modifies the selected menu.

The monitoring device according to the present invention also comprises a blank module. During the sampling cycle, a blank sample is collected. An additional inlet, only used for blank sampling, is present in the monitoring device. The inlet is connected to said blank module, which contains a filter and an absorbent to trap compounds in order to ensure clean reference air. The device gives a certain response for a certain concentration of the analyte. To translate the response to concentration information about the calibration curve need to be present. The calibration curve can be linear or more complex. The intercept can pass through the origin or not. To know about the intercept a blank sample need to be analysed in order to have a valid calibration curve for the translation of the electrical response into concentration.

The monitoring device according to the present invention is to be enclosed in a casing. Said device can be used as a handheld device, but can also be placed at a site with a certain holder or clamped to e.g. a tripod. It can also be carried with a belt clip or harness. The pump(s) will be IECEx certified and ATEX approved for use in explosive environments. The pump will have one connector exposed, i.e. a USB connector. The USB connector serves for wired communication and charging. When using the device in explosive areas this connector will be covered by a dust, air and water tight seal. The display of the pump will be covered behind a transparent surface that conforms to the IECEx and ATEX requirements. Thus, a direct reading device for improved qualitative and quantitative monitoring of airborne compounds present in both gas and particle phase is provided. The monitoring device can also be used for compounds on surfaces or in a matrix that can be made volatile by e.g. heating.

The usage of the pump when sampling covers typically five scenarios:

1) Manual Sampling:
The device is turned on. Via a graphical user interface, the desired flow is set to a certain amount of ml/min.

The pump is programmed via the user interface to stop after a certain time. The pump is then started via a graphical user interface. The pump control system maintains a flow as close as possible to the desired flow. The pump is stopped (manually if not pre-programmed) after a certain time.

2) Preset Sampling:
The device is pre-programmed on a computer via USB. On startup of the device the user can select "run predefined sampling", whereas the pump runs at a certain flow for a certain time, then stops.

3) Slave Mode:
The pump is placed at a site, and can be controlled remotely via a computer application or from another pump device configured for controlling other pumps remotely. This mode can also be used in laboratory environments where an arbitrary number of pumps can be controlled simultaneously, and where schedules for sequential sampling may be set up in the computer application.

4) Transferring Logged Data:
The pump is switched on and connected to a computer via USB. The pump is administered via a computer application. Via the application one or several of the pump device's log files can be transferred to the computer and/or deleted from the pump device's memory.

5) As Component in Other Devices:
This assembly is a solution for acquiring a stable volumetric flow and can be used as a module or component in any device where generation of a stable flow is needed.

According to one embodiment of the present invention the detection unit contains an ion filter (DMS). The separation of the different analytes in the air flow is based on their volatility prior the ion filter, i.e. in the chromatography unit.

A focusing trap is added prior a chromatographic column. When the analytes have been thermally desorbed from the sampling device, either for a separate or a total analysis, and then have been trapped in one or more enrichment traps 1, the analytes are then thermally desorbed from each enrichment trap 1. They will then be in a smaller gas volume than from the sampling device, and a focusing effect is achieved prior entering the chromatography unit, such as a GC column. The use of enrichment traps reduces the peak width and increase the peak symmetry in the GC chromatogram, resulting in lower detection limits and improved repeatability.

In the ion filter embodiment of the detection unit system according to the present invention, ionisation of the chromatographically separated analytes is performed prior entering the ion filter (DMS). More precisely, the analytes eluted from the chromatographic column is ionised. A stable and reproducible ionisation is necessary for accurate monitoring. An ionisation technique based on e.g. photo ionisation, $Ni^{63}$ ionisation etc. is used.

For sufficient selectivity an additional separation of the ionized analytes needs to be performed with a view to separating and detecting the ionized compounds based on their differential motilities at the low parts per trillion-region. For this purpose a microDMx™ sensor chip (Sionex Inc., Bedford, Mass., USA) may be used.

As explained above problems with memory effects, i.e analyte carry over, may occur during sampling of concentration peaks. The present inventors have solved this problem by the introduction of an air flushing step, wherein the sampling device, the enrichment traps, and all connections and tubing needs are flushed between sampling cycles. The flushing is performed to ensure that no relevant carry over occur. If the analysis of a blank sample indicates that there is a carry over the flushing parameters (flow speed, duration etc.) are adjusted to until no carry over is observed.

As appears, the flow regulating system and the monitoring device according to the present invention has several advantages and differences compared to present known techniques. One important difference compared to known methods is that the sample introduction to the mass separator and/or mass filter (the sampling device) and/or ion filter and/or mass spectrometer and/or gas chromatograph and/or detector and/or analyser is made in such a way that both gas and particle borne compounds are collected, desorbed and determined in a quantitative and qualitative way. Further, automatic volumetric sampling is enabled by the sampling device. Reactive compounds, i.e. analytes, e.g. isocyanates, isothiocyanates, aldehydes, amines anhydrides etc., and compounds containing functional groups that can be derivatised to volatile compounds that can be analysed and determined, are collected and derivatised to stabile derivatives and desorbed and analysed by the active reactive sampling device. Valid results are obtained by automatic field calibration and sampling is checked for breakthrough. Carry over compounds and memory effects are checked by the automatic analysing of blanks. Drawbacks in linearity are compensated for by the adjustment of the sampling time to achieve sample concentrations in the linear range.

EXAMPLE 1

Figure 9:
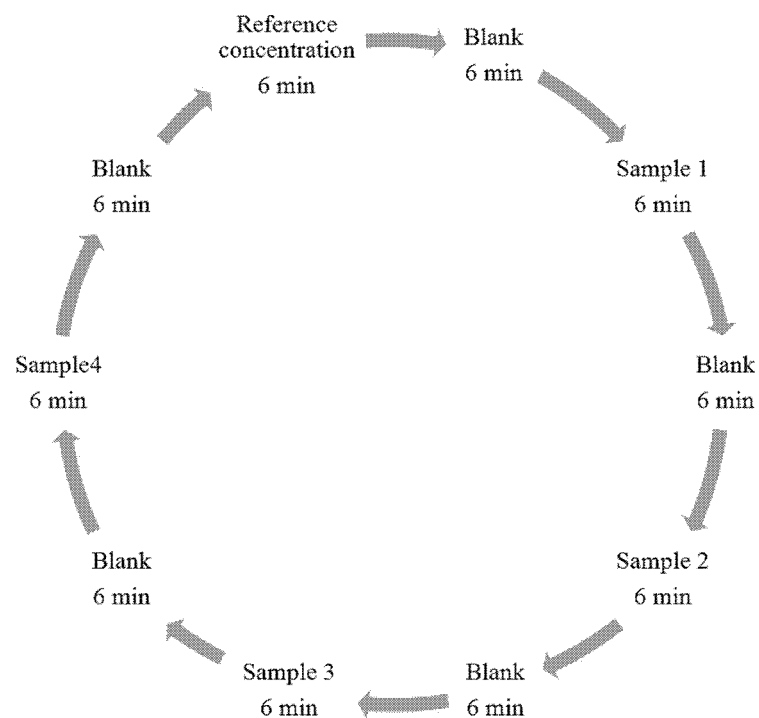
FIG. 9 shows an example of a sampling sequence used in the method according to the present invention.

FIG. 9 shows an example of a measurement cycle for a volatile analyte compound. The GC-DMS system used in this embodiment monitors the analyte concentration and alternates between monitoring of concentration of the analytes, the blank, and a reference.

EXAMPLE 2

Figure 10:
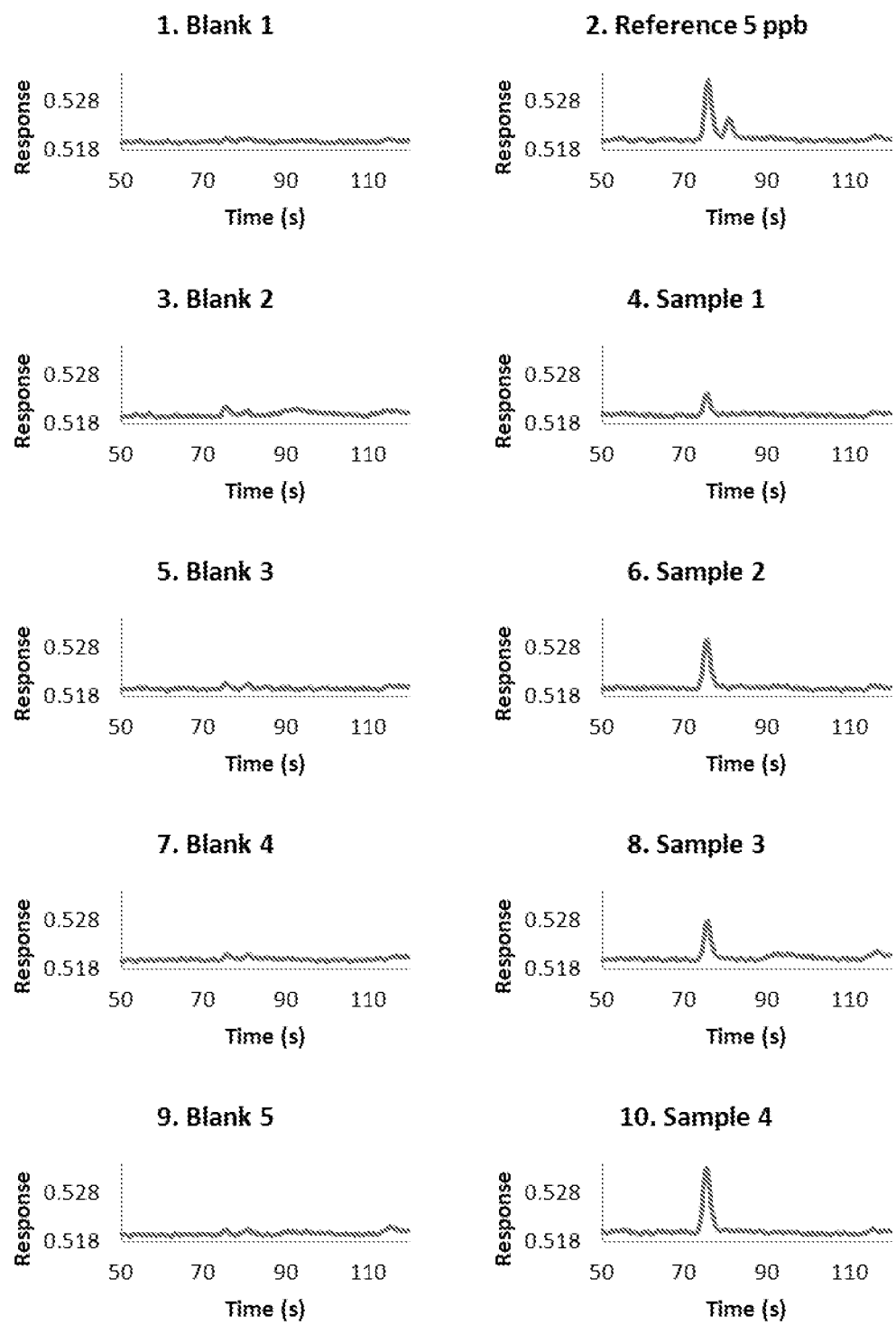
FIG. 10 shows GC-DMS chromatograms from a sampling sequence.

FIG. 10 shows an example of GC-DMS chromatograms from a sampling sequence of 4 samples containing different concentrations of benzene and a reference containing 5 ppb of benzene. The samples are taken from four different tubing located at different positions in a system. After each collection of a sample to the sampling system a blank sample is taken. The figure shows that no memory effects or carries over from a sample or a reference sample is observed in the blank samples. In reference 5 ppb it can be observed that an additional chromatographic peak is observed. This peak in not benzene, but it is an unknown compound. The chromatographic resolution is necessary to distinguish the analyte (benzene) from other components that may be present.

EXAMPLE 3

Figure 11:
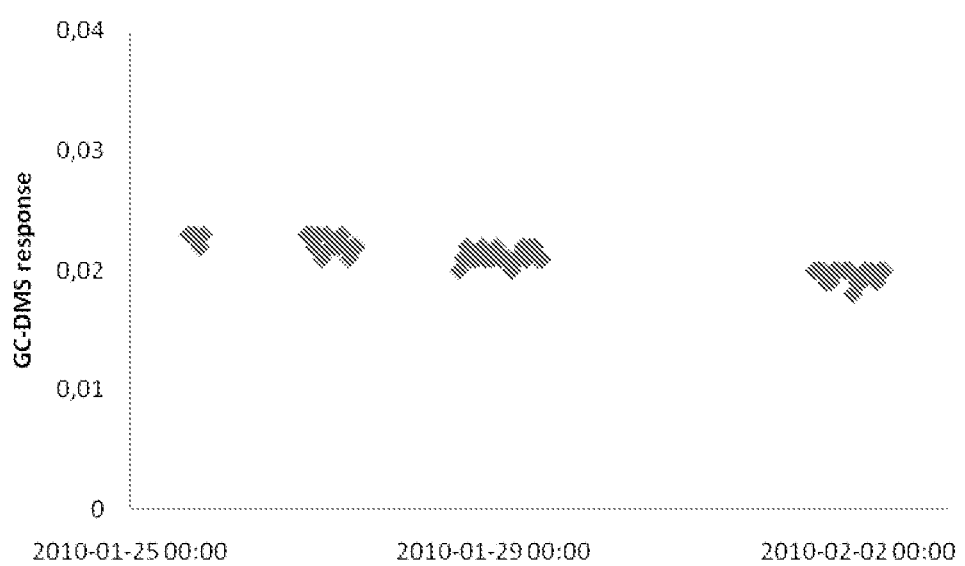
FIG. 11 shows the GC-DMS responses from repeated benzene measurements.

FIG. 11 shows the GC-DMS response for benzene (5 ppb) for 59 measurements during a period of two weeks. The variation (RSD) was <6%. The figure shows that the response varies with time and there is a trend that the response decreases with time. It demonstrates that the instrument needs to be calibrated in order to get valid estimation of the concentration. The drift in response is due to drift in the set parameters for the ion source, mass separator (DMS) and the detector. It may be due to electronic drift and contamination of electrodes and/or differences in conditions due to a variation in conditions for the gas flow (humidity, flow speed etc.) The figure shows the need for field calibration and tuning and that factory set parameters are insufficient to get valid results.

EXAMPLE 4

Figure 12:
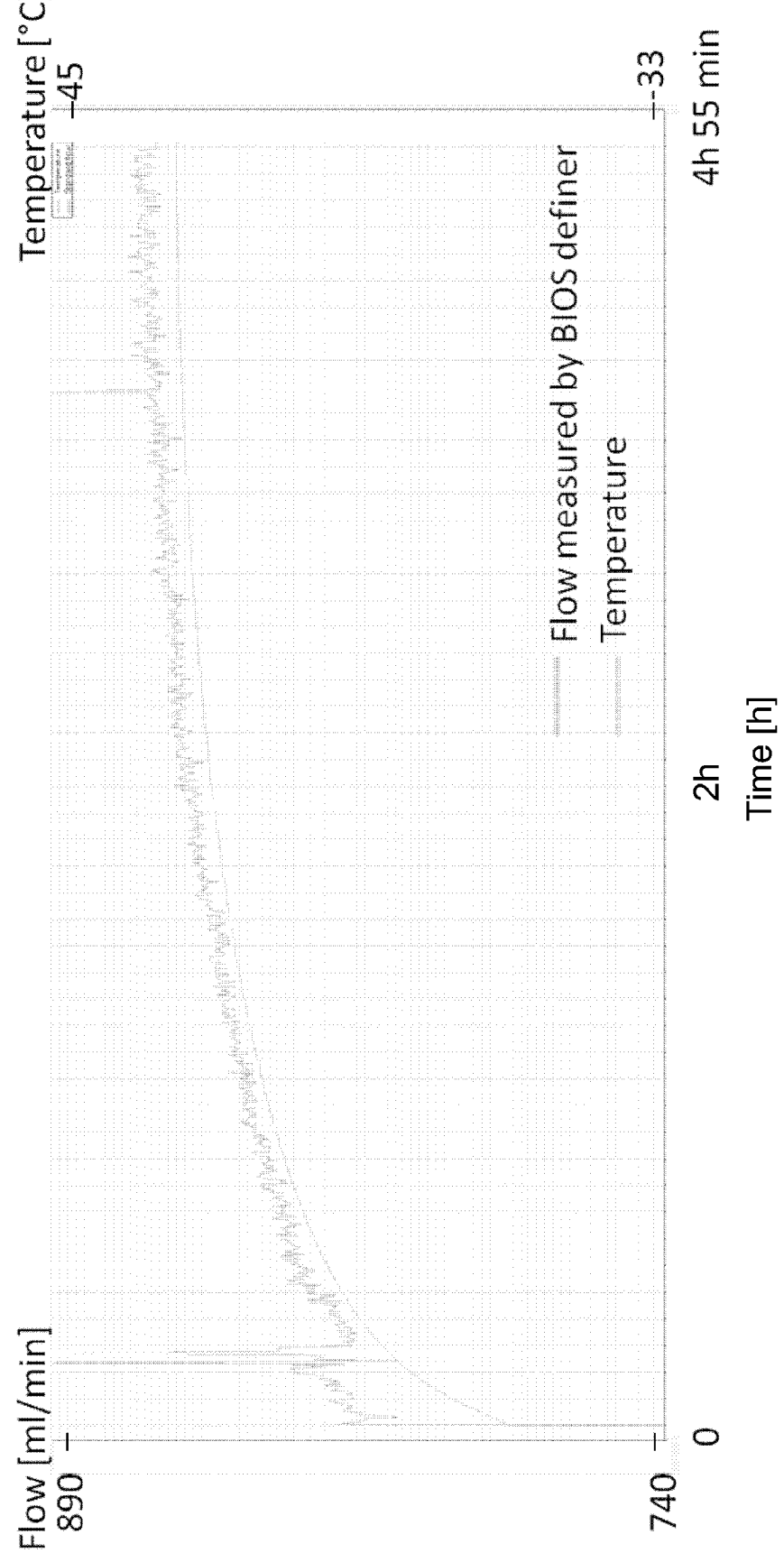
FIG. 12 shows the temperature response of a thermal differential flow sensor.

FIG. 12 shows the temperature response of a thermal differential flow sensor. To investigate the temperature drift of a thermal differential flow sensor the thermal differential flow sensor was placed in a temperature controlled environment and fed with a constant well-known mass flow. The actual flow was held constant and was measured using another flow meter, not affected by temperature. In FIG. 12, the voltage output from the mass flow sensor has been converted to a volumetric flow according to the mass flow meter calibration data. As can be seen in FIG. 12, the measured flow is affected very much by temperature. An increase in measured flow from 818 ml/min to 866 ml/min, i.e. an increase of approximately 6%, can be noted when rising the sensor temperature from 3° C. to 28° C. Thus, it is important to compensate for the sensor temperature to be able to produce accurate and precise measurement results. A number of measurement results as done in FIG. 12, i.e. when altering the sensor temperature while measuring the actual flow through the flow meter, can later be used as a calibration curve to compensate for the sensor temperature in real measurements using the flow regulating system. This calibration procedure is also repeated for different flows to compensate for different temperature dependency of the mass flow sensor electronics at different flow levels.

REFERENCES

Schneider B B, Covey T R, Coy S L, et al, Control of chemical effects in the separation process of a differential mobility mass spectrometer system, EUROPEAN JOURNAL OF MASS SPECTROMETRY, 2010, 16(1), 57-71

Krylov E V, Nazarov E G, Electric field dependence of the ion mobility, 2009, INTERNATIONAL JOURNAL OF MASS SPECTROMETRY, 285(3), 149-156

Krylov E V, Coy S L, Nazarov E G, Temperature effects in differential mobility spectrometry, INTERNATIONAL JOURNAL OF MASS SPECTROMETRY, 2009, 279(2-3), 119-125

Krylov E V, Nazarov E G, Miller R A, Differential mobility spectrometer: Model of operation, INTERNATIONAL JOURNAL OF MASS SPECTROMETRY, 2007, 266(1-3), 76-85

Kendler S, Lambertus G R, Dunietz B D, et al., Fragmentation pathways and mechanisms of aromatic compounds in atmospheric pressure studied by GC-DMS and DMS-MS, INTERNATIONAL JOURNAL OF MASS SPECTROMETRY, 2007, 263(2-3), 137-147

Marand Å, Karlsson D., Dalene M., Skarping G., Solvent-free sampling with di-n-butylamine for monitoring of isocyanates in air, J. Environ. Monit., (2005), DOI: 10.1039/B414761H.

The invention claimed is:

1. A flow regulating system for maintaining a stable gas flow comprising
   at least one pump,
   at least one mass flow sensor,
   an ambient temperature sensor,
   an ambient pressure sensor,
   a back pressure sensor, and
   a control system,
      wherein the input from said sensors to said control system is adapted to regulate the at least one pump to keep a stable mass flow.

2. The flow regulating system according to claim 1, wherein said control system includes a computer.

3. The flow regulating system according to claim 1, wherein said at least one pump is a rotary vane pump.

4. The flow regulating system according to claim 1, comprising two or more mass flow sensors.

5. The flow regulating system according to claim 1, wherein at least one of said at least one mass flow sensor is a thermal differential flow sensor.

6. The flow regulating system according to claim 1, further comprising an ambient humidity sensor having an output, wherein the output from said ambient humidity sensor is connected to said control system.

7. The flow regulating system according to claim 1 further including a computer and sources data for one or more of GPS position, power consumption, battery level, and time, the system further comprising a logging function executable by the computer for logging one or a combination of the values contained in the group:
mass flow, back pressure, ambient temperature, ambient pressure, ambient humidity, mass flow sensor temperature, GPS position, power consumption, battery level, and time.

8. The flow regulating system according to claim 1, further comprising a graphical display and a user interface displayed on said graphical display.

9. The flow regulating system according to claim 1, further comprising user navigational means for adjusting flow regulating system settings.

10. The flow regulating system according to claim 1, further comprising connection means for connecting said flow regulating system to an external electronic device.

11. The flow regulating system according to claim 10, wherein said external electronic device is one of the electronic devices contained in the group consisting of:
a personal computer, a handheld computer, a smartphone, and a digital memory device.

12. The flow regulating system according to claim 1, further comprising a diagnostic system utilizing a first input signal-from said back pressure sensor, a second input signal from said mass flow sensor and a third input signal in the form of a control signal applied to said at least one pump, said first, second and third input signals being employed by the diagnostic system to assess the mechanical condition of one or more components of the flow regulating system.

13. A cluster of flow regulating systems wherein at least two flow regulating systems according to claim 1, are connected in series or in parallel.

14. A method for measuring a flow using a flow regulating system according to claim 1, wherein the method comprises the steps of:
measuring the mass flow with the at least one mass flow sensor,
adjusting the mass flow measurement value according to a predetermined calibration of temperature related error, and
calculating a volumetric flow from said mass flow measurement using the measured mass flow, the ambient temperature, and the ambient pressure.

15. The method for measuring a flow according to claim 14, wherein the at least one mass flow sensor provides at least one analog output signal, the method further comprising the step of
converting the at least one analog output signal from the at least one mass flow sensor to at least one digital signal.

16. The method for measuring a flow according to claim 14, further comprising the step of one or both of monitoring and logging flow pulsation using the at least one mass flow sensor.

17. The method according to claim 14, further comprising the steps of:
obtaining a measurement of a current back pressure using the back pressure sensor; and
compensating for errors in said mass flow measurement due to the current back pressure by adjusting the mass flow measurement value by a predetermined increment depending on said measured current back pressure.

18. The method according to claim 14, further comprising the step of one or both of monitoring and/or logging flow pulsation using the back pressure sensor.

19. The method according to claim 14, wherein the at least one mass flow sensor or the back pressure sensor provide an output signal indicative of flow pulsation, the method further comprising the step of introducing a cancellation pulse to reduce or cancel said flow pulsation.

20. A method for measuring a flow according to claim 14, wherein the method further comprises the steps of:
measuring the temperature of the at least one mass flow sensor using a temperature compensation sensor, and
adjusting the mass flow measurement value according to a predetermined calibration of temperature related error and the measured temperature from said temperature compensation sensor.

21. A device for the monitoring of air-borne compounds present in one or both of a gas phase and a particle phase within an air flow, the device for the monitoring of air-borne compounds comprising a sampling device, an enrichment trap, a calibration and tuning module, a blank module, said flow regulating system according to claim 1, a chromograph, and a detection unit.

22. The monitoring device according to claim 21, wherein the sampling device comprises a sampling tube having an inlet for the air flow and having the ability to absorb an analyte in the gas phase of said air flow, a filter downstream of the the sampling tube in said air flow and having the ability to absorb an analyte in the particulate phase within said air flow, and a sorbent downstream of the filter and having the ability to absorb any analytes in a gas phase which have passed through the filter.

23. The monitoring device according to claim 22, wherein the enrichment trap is connected to each of the sampling tube, the filter and the sorbent for separate detection of analyte released from said sampling tube, filter, and sorbent, respectively, or connected to only the sorbent for detection of analyte released from the sampling device.

24. The monitoring device according to claim 21, wherein the sampling device comprises a first sorbent having an inlet for the air flow and having the ability to absorb the analyte in the gas phase of said air flow, a filter connected to the first sorbent and having the ability to absorb the analyte in the particle phase of said air flow, and a second sorbent connected to the filter and having the ability to absorb any analyte which has passed through the filter.

25. The monitoring device according to claim 24, wherein an enrichment trap 1 is connected to each of the first sorbent, the filter and the second sorbent for separate detection of analyte released from said first sorbent, filter, and second sorbent, respectively, or connected to only the second sorbent 6 for total detection of analyte released from the sampling device.

26. The monitoring device according to claim 21, wherein the sampling device is a particle size selective sampling device comprising a pre-selector to remove large particles, a denuder to collect gas phase analytes, an impactor to separate larger particles from inhalable or respirable sizes and a filter to collect inhalable or respirable particles.

27. The monitoring device according to claim 21, further including a computer, wherein the calibration and tuning module is insertable and detachable from the monitoring device, is connected with the sampling device, and is controlled by the computer to calibrate and tune the monitoring device using at least one reference analyte.

28. The monitoring device according to claim 27, further including a heating device, wherein said calibration and tuning module comprises a closed tube containing the at least one reference analyte and the closed tube is surrounded by the heating device.

29. The monitoring device according to claim 21, wherein the blank module is connected to the sampling device, has a separate inlet to the monitoring device, and comprises a filter and a sorbent.

30. The monitoring device according to claim 21, wherein said at least one pump in said flow regulating system is present between the enrichment trap and the chromatograph.

31. The monitoring device according to claim 21, wherein the chromatograph comprises a gas chromatograph.

32. The monitoring device according to claim 21, wherein said detection unit is a differential mobility spectrometry detector, a gas chromatography detector or a direct reading detector.

33. A method for the detection of air-borne analytes in an airflow by use of the monitoring device as claimed in claim 21, comprising the following consecutive steps:
    a) inserting one or more different calibration and tuning modules containing different analyte references into the monitoring device,
    b) introducing the air flow containing the air-borne analytes and a reagent in the sampling device to be reacted with each other therein,
    c) heating the sampling device containing the sampling tube, the filter and the sorbent, or the first sorbent, the filter, and the second sorbent, to release analytes adsorbed in the sampling device,
    d) collecting the analytes released from said sampling device in one or more enrichment traps,
    e) analysing the analytes using the chromagraph,
    f) detecting the analytes quantitatively and qualitatively.

34. The method according to claim 33, wherein after the detection of each analyte performing steps a)-f) on a blank.

35. The method according to claim 34, further including the step of flushing the monitoring device with air to eliminate any memory effects from analytes and other compounds which have passed through said monitoring device.

36. The monitoring device according to claim 21, wherein said at least one pump in said flow regulating system is present between the sampling device and the enrichment trap.

37. A flow regulating system according to claim 1, further comprising a temperature compensation sensor for measuring the temperature of said at least one mass flow sensor.

38. The flow regulating system according to claim 37, wherein:
    said control system includes a computer;
    said at least one pump is a rotary vane pump controlled by at least one pump control signal;
    said at least one mass flow sensor includes at least two mass flow sensors;
    at least one of said at least two mass flow sensor is a thermal differential flow sensor; and said flow regulating system further includes:
    an ambient humidity sensor having an output, wherein the output from said ambient humidity sensor is connected to said control system;
    a logging function executable by said computer for logging one or a combination of the values contained in the group:
        mass flow, back pressure, ambient temperature, ambient pressure, ambient humidity, mass flow sensor temperature, GPS position, power consumption, battery level, and time;
    a graphical display and a user interface displayed on said graphical display by said computer
    the graphical display including user navigational means for adjusting flow regulating system settings;
    connection means for connecting said flow regulating system to an external electronic device,
    wherein said external electronic device is one of the electronic devices contained in the group consisting of:
        a personal computer, a handheld computer, a smartphone, a digital memory device; and
    a diagnostic system utilizing a first input signal from said back pressure sensor, at least one second input signal from said at least two mass flow sensors and at least one third input signal corresponding to the at least one pump control signal to assess the mechanical condition of one or more components of the flow regulating system.

39. The method for measuring a flow according to claim 20, wherein the at least one mass flow sensor provides an analog output signal and the at least one mass flow sensor or the back pressure sensor provide an output signal indicative of flow pulsation, the method further comprising:
    converting the analog output signal from the at least one mass flow sensor to at least one digital signal;
    one or both of monitoring and logging flow pulsation using the at least one mass flow sensor;
    measuring a current back pressure with said back pressure sensor;
    compensating for errors in said mass flow measurement due to the current back pressure by adjusting the mass flow measurement value by a predetermined increment depending on said measured current back pressure;
    monitoring flow pulsation using the back pressure sensor; and
    introducing a cancellation pulse to reduce or cancel said flow pulsation.

* * * * *